United States Patent [19]

Skjervold

[11] Patent Number: 4,970,146

[45] Date of Patent: Nov. 13, 1990

[54] METHOD OF DETERMINING ABSORBED NUTRIMENT IN LIVING ORGANISMS

[75] Inventor: Harald Skjervold, Ås, Norway

[73] Assignee: Havbrukskjemi A/S, Oslo, Norway

[21] Appl. No.: 102,564

[22] Filed: Sep. 11, 1987

[51] Int. Cl.$^5$ .................. C12Q 1/00; G01N 21/77
[52] U.S. Cl. .................. 435/29; 250/282; 356/316; 435/35; 435/807; 436/20; 436/56; 436/57; 436/82
[58] Field of Search .............. 436/20, 56, 57, 82; 435/29, 35, 807; 250/282; 356/316

[56] References Cited

U.S. PATENT DOCUMENTS

| | | | |
|---|---|---|---|
| 3,716,631 | 2/1973 | Steggerda et al. | 424/9 |
| 3,818,089 | 6/1974 | Bayley et al. | 424/9 |
| 4,283,382 | 8/1981 | Frank et al. | 436/546 |
| 4,392,236 | 7/1983 | Sandstrom et al. | 119/3 |
| 4,421,858 | 12/1983 | Jackson | 436/56 |
| 4,735,907 | 4/1988 | Schaeffer et al. | 436/546 |

*Primary Examiner*—Robert J. Warden
*Assistant Examiner*—Jill Johnston
*Attorney, Agent, or Firm*—Robert E. Burns; Emmanuel J. Lobato

[57] ABSTRACT

A method of determining the amount of nutriment absorbed in living organisms comprising animals, fish and plants comprises adding to the animal, fish or plant food one or more elements from the lanthanide series as tracers. After the nutriment has been absorbed, a sample is taken from a localized part of the living organism, for example a fish scale, and the sample is analyzed by ICP (inductively coupled plasma) to determine the amount of tracer and thus the amount of absorbed nutriment in the living organism.

4 Claims, No Drawings

METHOD OF DETERMINING ABSORBED NUTRIMENT IN LIVING ORGANISMS

The present invention relates to a method of determining the absorption by organisms, human beings, animals and plants, when a predetermined amount of one or more tracers is added to food.

The invention, furthermore, relates to utilization of such tracers for determining absorption of nutrition.

In recent times, a constantly rising demand for economizing on the available resources of nutrition of the earth was brought to light. A very important factor in such an improved utilization of the resources of nutrition is the ability of the recipient to benefit from the food.

With a reliable method of determining the absorption of nutrition by domestic animals and fish, i.e. the ability of utilizing received feed during a given period of time, it would be possible to obtain breeding animals which could then be used for breeding with a view to obtain herds/flocks having a lower feed consumption, but a higher carcass weight having higher energy content or other properties. The importance of this may be illustrated by the fact that pigs having a carcass weight of 90 kg used an average of approximately 220 kg feed, whereas the extreme values may be between 170 and 270 kg.

Among known methods of marking fish, the previously most used, the Carlin method, has obvious drawbacks, being in the first place probably a handicap to the fish. Additionally, it is demanding and hazardouso, since the marks may get lost. In a recent effort to mark fish, especially in connection with letting out large quantities of salmon fry in the USA and in Canada, small coded metal chips were used that were placed in the fish heads. By the aid of detectors it is then possible to decide which fish is marked. It is, however, a disadvantage that said metal chips must be removed by surgery in order to be closely identified, and that makes slaughtering necessary.

Determination of the utilization of energy in nourishment also necessitates slaughtering, and then the animal can, obviously, not be used for breeding.

The simplest method, weighing absorbed feed, is practically impossible, since most animals are fed in herds so that the feed administered would have to be based on the average value. This might, of course, be avoided by individual feeding of each animal. There are, however, practical problems in connection with such an approach as well, since it would be impossible to carry out both from economical reasons and due to the time consumption involved. Also, the problem would arise that many animals do not consume equally whether they are alone or in a herd.

There is, thus, a great and widespread demand for a method which can, in a reasonably reliable manner, indicate how large an amount of feed the animal has taken during a given period of time, without a necessity of slaughtering the animal to obtain a close identification of the period of feeding and the category of feed, at the same time as there should be no physical disadvantages to the animal.

The concept on which the present invention is based is that certain chemical elements or the like are enriched and/or accumulated in the body if they are taken with nutrition. An analysis of these elements could, thus, theoretically form a basis for recording the absorption of nutrition if said element were added to the nutrient in a predetermined amount.

The flaw of this method, however is that most elements of interest are already present both in feed and in organisms, and this would cause a quite essential source of error in a later analysis.

There are, however, certain elements that are quite scarce and are only found in rather negligible amounts in large areas of the earth. These elements belong to the so called rare-earth elements, inter alia lanthanides, i.e. elements belonging to group 3b of the periodic system and, more precisely, elements with atomic numbers 57 to 71, that is the elements lanthanum, cerium, prasecdymium, neodymium, promethium, samarium, europium, gadolinium, terbium, dysprosium, holmium, erbium, thulium, ytterbium, and lutetium, as well as the remaining group 3b elements scandium with number 21, and uttrium with number 39.

At an earlier time tests were made with adding selected ones of the above stated elements to fish feed in connection with an experiment of marking salmon.

In connection with said experiment oxides of the elements ytterbium, terbium, dysprosium, and samarium were used as start materials. Said oxides were transferred into nitrates and mixed into the feed of salmon fry according to certain determined methods of dosing. After a year at sea fish-scale samples were taken from salmon of the same age which had not received marked feed.

According to the methods available at that time said scale samples were activated to make all used elements radioactive. After that the amount of said four elements that were normally not expected to be present in this fish was detected by special measuring instruments.

TABLE I

| Scale samples from | Ytterbium | Terbium | Elements Dysprosium | Samarium |
|---|---|---|---|---|
| "Marked fish (fed lanthanides | 1.151 | 0.717 | 1.568 | 1.437 |
| Control group | 0.026 | 0.01 | 0.005 | 0.017 |
| Increase of concentration, nomb, times | 44 | 72 | 314 | 84 |

The table clearly shows that the marking method results in highly significant manifestations.

If there had, thus, been relatively inexpensive and rapid methods of taking readings from such scale samples, a marking method would have been achieved permitting many variants, i.e. $2^n - 1$, n representing the number of foreign elements added to the feed. Marking itself is very simple, as will be understood.

As indicated above, this method of measuring could not be carried out in practice at first, because of time consuming and expensive analyses.

Recently, however, new measuring instruments for detecting elements have been developed, radioactivation not being necessary. By the aid of ICP, or inductively coupled plasma, amounts of up to 50 elements/minute of each sample may be read. If especially "easily read" elements are selected, there is also somewhat less expensive equipment able to read the quantity of elements with very high accuracy, up to parts per billion.

Consequently, it is possible to overcome the drawbacks to he know technology, and the present invention, thus, relates to a method for determining the absorption of nutrition or other desired test readings in farm animals and fish, or other organisms and said method is characterized by the fact that a predetermined amount of one or more racer(s) not naturally occurring in the feed or the animal is added to the feed, and that selected samples from the live animal, e.g. hair, scale, fragments of skin, fins, hooves, etc. are analyzed with a view to the total accumulated amount of tracer(s), and that the the amounts of nutrition absorbed during a given period of time, or other desired test readings are determined on the basis of said analysis.

The invention also relates to utilization of one or a number of elements from the lanthanide series per se or in any state, shape, mixture, or combination, as tracer(s) in the above stated method for determining the absorption of nutrition by fish or farm animals.

The method according to the invention has a series of advantages. Since readings are very accurate, only minimum amounts have to be added to the feed. Assuming a limit of demonstrability at 0.005 mg/liter and assuming that a salmon reaches 5 kg before sampling, 1 gram will theoretically be sufficient for marking 2000 smolt. If the tracer selected is samarium with a price per gram of NOK 6.—marking per se will only represent negligible expenses.

Since reading may possible be made less expensive with use of other elements than those indicated above, utilization of the lanthanide series, however, ensures special advantages. If, e.g. 8 different elements are selected, these may be used in 263 different combinations, and this ensures wide possibilities of dividing test animals into groups with a view to feed mixtures and age groups.

The essential consideration in selecting said rare-earth elements is, however, that they accumulate or deposit to such a degree that they may, e.g. in full-grown fish, be identified with available measuring methods, and that the necessary additions in feed will have no undesirable secondary effects.

Even though the invention is disclosed with reference to fish, and especially salmon, it can, obviously, be used in the same manner for all kinds of domestic animals.

The present invention, thus, makes available a novel method with unsurpassed accuracy for determining the total absorption of nutrition in domestic animals and fish, permitting analyses to be made very rapidly and without tormenting the animal.

I claim:

1. A method of determining absorbed nutriment in living organisms, which comprises adding one or more elements from the lanthanide series in the periodic system of elements, alone or in combination, as tracer(s) in nutriment, allowing the nutriment to become absorbed in the living organism, taking samples from localized parts of said living organism, analyzing said samples with a view to determining the total absorbed amount of tracer through use of ICP (inductively coupled plasma) and determining the amount of absorbed nutriment in said living organism on the basis of said analysis.

2. A method according to claim 1, wherein said tracers are selected from the group consisting of ytterbium, terbium, dysprosium and samasium.

3. A method according to claim 1, wherein a plurality of said tracers are used in different combinations in respective organisms to identify selected organisms.

4. A method of determining absorbed nutriment in an animal which comprises adding at least one element from the lanthanide series in the periodic system of elements as a tracer in animal nutriment, feeding said nutriment containing said tracer to an animal, allowing said nutriment to become absorbed in tissues of said animal, taking samples from localized parts of said animal and analyzing said samples to determine the amount of tracer therein as an indication of the amount of absorbed nutriment.

* * * * *